United States Patent
Cabauy

(10) Patent No.: US 11,270,807 B2
(45) Date of Patent: *Mar. 8, 2022

(54) SMALL FORM FACTOR BETAVOLTAIC BATTERY FOR USE IN APPLICATIONS REQUIRING A VOLUMETRICALLY-SMALL POWER SOURCE

(71) Applicant: CITY LABS, INC., Miami, FL (US)

(72) Inventor: Peter Cabauy, Miami, FL (US)

(73) Assignee: CITY LABS, INC., Miami, FL (US)

( * ) Notice: Subject to any disclaimer, the term of this patent is extended or adjusted under 35 U.S.C. 154(b) by 155 days.

This patent is subject to a terminal disclaimer.

(21) Appl. No.: 16/588,000

(22) Filed: Sep. 30, 2019

(65) Prior Publication Data

US 2020/0043623 A1   Feb. 6, 2020

Related U.S. Application Data

(63) Continuation of application No. 15/589,665, filed on May 8, 2017, now Pat. No. 10,431,345, which is a
(Continued)

(51) Int. Cl.
| | |
|---|---|
| *G21H 1/02* | (2006.01) |
| *A61N 1/378* | (2006.01) |
| *H01M 10/46* | (2006.01) |
| *G21H 1/06* | (2006.01) |
| *H01M 10/052* | (2010.01) |
| *H01M 10/0562* | (2010.01) |

(52) U.S. Cl.
CPC .............. *G21H 1/02* (2013.01); *A61N 1/378* (2013.01); *A61N 1/3787* (2013.01); *G21H 1/06* (2013.01); *H01M 10/46* (2013.01); *H01M 10/052* (2013.01); *H01M 10/0562* (2013.01); *H01M 2220/30* (2013.01)

(58) Field of Classification Search
None
See application file for complete search history.

(56) References Cited

U.S. PATENT DOCUMENTS

| | | | |
|---|---|---|---|
| 3,924,137 A | 12/1975 | Mger | |
| 8,487,501 B2 * | 7/2013 | Oka | ........................ H02K 3/345 310/215 |

(Continued)

OTHER PUBLICATIONS

Kavetskiy, et al., "Tritium Battery with Solid Dielectric", Nuclear Science and Engineering, 2011, pp. 172-179, vol. 168, Trace Photonics, Inc., Charleston US.
(Continued)

*Primary Examiner* — Daniel S Gatewood
(74) *Attorney, Agent, or Firm* — John L. DeAngelis; Wolter, Van Dyke, Davis, PLLC

(57) ABSTRACT

A betavoltaic power source. The power source comprises a source of beta particles and a plurality of regions each for collecting the beta particles and for generating electron hole pairs responsive to the beta particle flux. A first set of the plurality of regions is disposed proximate a first surface of the source and a second set of the plurality of regions is disposed proximate a second surface. The first and second surface in opposing relation. A secondary power source is charged by a current developed by the electron hole pairs.

16 Claims, 3 Drawing Sheets

Related U.S. Application Data continuation-in-part of application No. 14/304,687, filed on Jun. 13, 2014, now Pat. No. 9,647,299.

(60) Provisional application No. 61/834,671, filed on Jun. 13, 2013.

(56) References Cited

U.S. PATENT DOCUMENTS

| | | |
|---|---|---|
| 8,487,507 B1 | 7/2013 | Cabauy |
| 2007/0088394 A1 | 4/2007 | Jacobson |
| 2007/0088396 A1 | 4/2007 | Jacobson |
| 2012/0101540 A1* | 4/2012 | O'Brien ............... A61N 1/3758 607/9 |
| 2013/0033149 A1 | 2/2013 | Thomas |

OTHER PUBLICATIONS

Honsberg, et al., "GaN Betavoltaic Energy Converters", IEEE Photovoltaics specialist conference, Jan. 2005, 1-4, Orlando US.

* cited by examiner

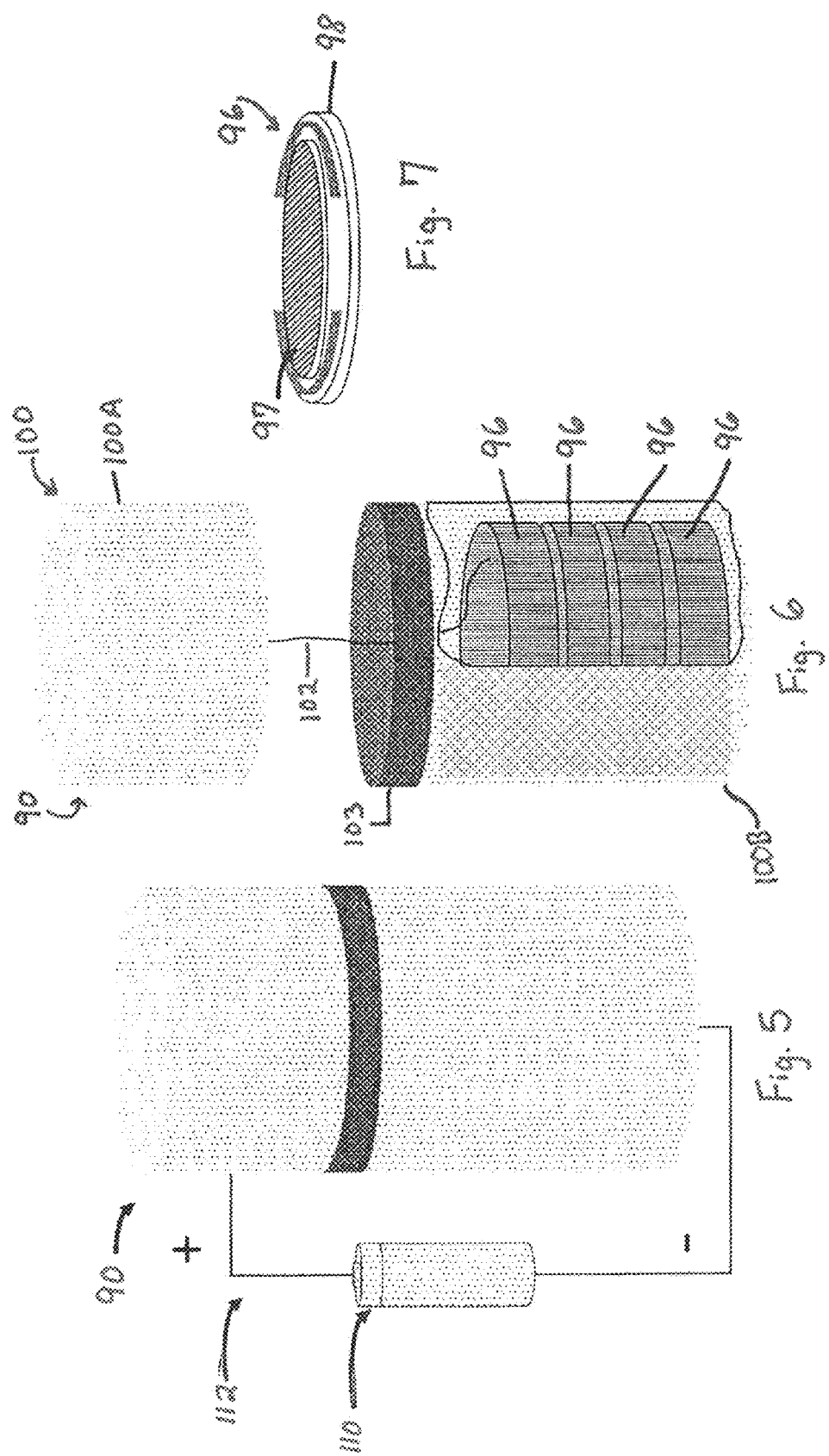

SMALL FORM FACTOR BETAVOLTAIC BATTERY FOR USE IN APPLICATIONS REQUIRING A VOLUMETRICALLY-SMALL POWER SOURCE

CROSS REFERENCE TO RELATED APPLICATIONS

The present application is a continuation of the application filed on May 8, 2017 and assigned application Ser. No. 15/589,665, and issued as U.S. Pat. No. 10,431,345, which is a continuation-in-part of parent application Ser. No. 14/304,687, filed on Jun. 13, 2014 and issued as U.S. Pat. No. 9,647,299, which claims priority under 35 U.S.C. 119(e) to the provisional patent application filed on Jun. 13, 2013 and assigned application No. 61/834,671. Each of the related applications is incorporated in their entirety herein.

FIELD OF THE INVENTION

The present invention applies to small form factor betavoltaic batteries especially for use with medical implants and in other applications where a small form factor is desired.

BACKGROUND OF THE INVENTION

Efforts aimed at miniaturization have always been a strong component associated with the advancements in the medical device/implant industry. In the $21^{st}$ century, this trend continues to be ever-present with a drive to scale down devices from a cubic centimeter range down to a cubic millimeter range. Smaller scale medical devices demonstrate great potential for reducing healthcare costs and mitigating trauma associated with invasive implant surgeries, while concomitantly improving both post-operative medical evaluations and convalescence periods.

The benefits of miniaturization are demonstrated with the emergence of a new class of cardiac pacemaker devices that are small enough to be inserted directly into a patient's right ventricle. The size reduction of these pacemakers and other medical devices is limited, in part, by the power sources that fuel the device's operation. Pacemaker batteries typically consume up to 40-80% of the device's volume. Consistent with this notion, further significant reductions in the scale of medical devices have been limited by the power sources themselves. While device components and electronic circuitry can be reduced to ever more diminutive dimensions, battery technology has traditionally remained limited to cubic centimeter dimensions arising as a consequence of exponential losses in energy density and capacity as batteries approach cubic millimeter scales. However, recent advancements in both electronics and battery technologies have led to reduced system power demands and higher power outputs from more diminutive power solutions.

Recent academic teams have laid the groundwork for an implantable cubic millimeter-scale device that can measure a glaucoma patient's intra-ocular eye pressure. This tiny device comprises a CMOS microcontroller that contains an on-board radio transmitter and sensor with cubic millimeter dimensions. The device operates at ultra-low power levels, e.g. picowatt power range during sleep cycles and at approximately microwatt power range during operational periods. Due to the extremely small dimensions of the device, it can be directly implanted within a patient's eye. The device can measure/record intra-ocular pressure throughout the day and radio-transmit processed data at periodic intervals to an external device for analysis.

This millimeter scale device utilizes an exceedingly small-sized solar cell to trickle-charge a millimeter scale LiPON (lithium phosphorous oxynitride) battery to provide a rechargeable power source. Such LiPON batteries are available from Cymbet Corporation of Elk River Minn., a manufacturer of small thin film, solid state secondary batteries. The Cymbet LiPON battery has approximately a 1 to 50 microamp-hour capacity, and the duty cycle of the device allows it to operate indefinitely as long as the solar cell provides an average of 10 nanoamps of current to the LiPON battery.

This configuration is well-adapted to an ocular implant where visible spectrum light energy is easily accessible and can be transmitted through the eye thereby providing the solar cell with the necessary trickle-charge power for the LiPON battery. However, such a solution is not suitable for implants that are not accessible to visible light, thereby rendering the solar cell component moot. An example of such a scenario might be a sensor embedded within a tumor for measuring pressure changes associated with tumor growth.

It should be noted that the LiPON battery can at best provide a maximum of 28 days of operation for implants in a stand-alone operation; this is far too short for most implantable devices that are not accessible to visible light sources. Clearly, a long-term (light-independent) trickle-charging source is required for maintaining the LiPON battery and subsequently facilitating operational effectiveness of such small-scale sensor systems operating with such a LiPON battery.

Unfortunately, chemical batteries with less than cubic centimeter dimensions have a less than optimal energy density. The optimal energy density for a lithium iodide battery in conventional pacemakers is approximately 1 watt-hour per cubic centimeter with a volume greater than about 3.0 cubic centimeters. To supply sufficient power to shrinking medical devices, an energy density of greater than about 1 watt-hour per cubic centimeter is desirable for battery volumes of approximately 0.5 cubic centimeters or less. In battery volumes of 0.1 cubic centimeters, a 10 watt-hour per cubic centimeter energy density would be highly desirable due to the loss of energy capacity in such a small volume (i.e. 1 watt-hour of capacity in a tenth of a cubic centimeter).

Furthermore, the battery needs to provide power in ranges from nanoamps to milliamps to accommodate duty cycle power requirements of medical device electronics. For example, wireless signals (to transmit the sensed values to an external device) require higher power bursts for short durations while the microcontroller's sleep power provides a low, but continuous drain. An ideal medical implant power source will have a high-energy density that is robust under a wide-range of power drains while having a diminutive form factor. Unfortunately, currently available betavoltaic power sources with less than 1 cubic centimeter dimensions will have only nano-watt to low-microwatt power outputs falling short of the required, or at least desired, higher power output necessary in some medical implant functions (e.g. radio telemetry, defibrillation etc.).

Betavoltaic power sources for medical device implants are not a new concept as they have a demonstrated potential for high energy densities well beyond conventional chemical batteries. Betavoltaic power sources do, however, suffer from low power densities and require radiation shielding. In the early 1970's, a group of researchers at Donald W. Douglas Laboratories of Richland, Wash. (led by Dr. Larry Olsen) invoked a promethium-147 radio-isotope to fuel a betavoltaic power source (also referred to as a Betacel) for energizing a cardiac pacemaker, which was successfully implanted in over 100 patients. Although the Betacel's size approximated 1.0 cubic inch, due to shielding requirements incurred from an associated gamma radiation emitting promethium-146 component, the successful implementation of this technology demonstrated the feasibility of betavoltaics for use within medical implants.

BRIEF DESCRIPTION OF THE FIGURES

The foregoing and other features of this invention will be apparent from the following more particular description of the invention, as illustrated in the accompanying drawings, in which like reference characters refer to the same parts throughout the different figures.

FIG. 5 illustrates a betavoltaic battery for charging a secondary power source.

FIG. 6 illustrates a cut-away view of the betavoltaic battery of FIG. 5.

FIG. 7 illustrates a beta source and beta collector of the battery of FIG. 5.

DETAILED DESCRIPTION OF THE INVENTION

Figure 1:
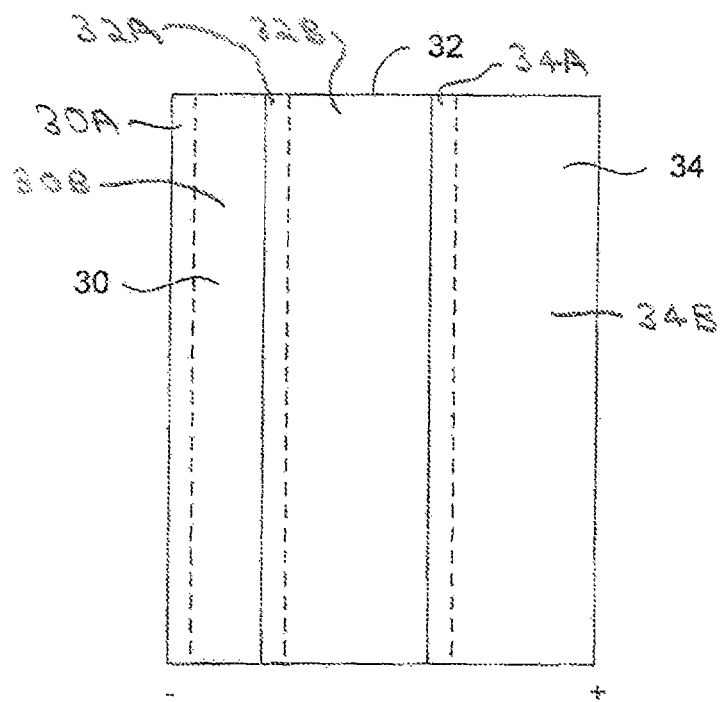
FIG. 1 illustrates a triple junction for use with the present invention.

In the teachings of the various embodiments of this invention, miniature betavoltaic power sources (with dimensions ranging from about a cubic millimeter to approximately 0.5 cubic centimeters) are constructed with energy densities approximately ranging from about 1 watt-hour per cubic centimeter to about 500 watt-hours per cubic centimeter, but the energy density may be more or less depending on the specific application. The energy density for a betavoltaic power source is calculated by integrating the betavoltaic device's power density over the medical device's useful life (e.g. 10 years for pacemakers). Betavoltaic power sources can be constructed in cubic millimeter volume spaces without negatively affecting the energy density; this is unlike conventional chemical battery technology where practical limitations exist in constructing micro-scaled cathodes, anodes, and liquid electrolyte volumes without incurring losses in energy density.

In the case of promethium, the inventors have discovered that the removal of the Pm-146 component is an important factor in reducing the shielding requirements for the betavoltaic battery. The gamma emission of Pm-146 is very high energy and is difficult to shield. The resulting shield requirements after removing the Pm-146 component are considerably less than the original BetaCel, as described above, that included the Pm-146 component with the Pm-147 component.

Tritium beta flux can be shielded with a thin sheet of paper, but the power density of tritium betavoltaic power sources of the prior art has been too low for use as a power source for medical electronics. It is only recently that betavoltaic cells with higher bandgap materials are able to achieve higher power densities when properly configured for use as high power-density betavoltaics. For example, combinations of thin betavoltaic cells (e.g. InGaP, InAlP, other III-V cells, SiC, or other betavoltaic cells), new high tritium density metal tritide films, and/or the use of enhanced surface area semiconductors (as described herein or in the referenced commonly-owned patent applications), the inventors have been able to approach energy densities of 1 watt-hour/cm^3 or greater and power densities in the range of 10's to 100's of microwatts/cm^3.

Betavoltaic power sources typically comprise a beta-emitting radioisotope affixed directly onto a semiconductor collector that is packaged in a container, which provides radiation shielding to levels appropriate for the intended application. The semiconductor collector material is similar to a solar cell and can easily be miniaturized to micro-scales without exhibiting losses in electrical properties, unlike conventional chemical batteries. Furthermore, radioisotopes such as tritium (H-3), promethium-147 (Pm-147), and nickel-63 (Ni-63) can all be incorporated into metallic forms, which can be similarly scaled to the semiconductor collector's dimensions.

In one embodiment of this invention, a betavoltaic power source with a volumetric dimension of approximately 0.5 cubic centimeters or less supplies power in the nanowatts to microwatts range and can provide nominal power in standby or active modes to medical implant circuitry.

In another embodiment of this invention, a betavoltaic power source with a volumetric dimension of approximately 0.5 cubic centimeters or less supplies power in the nanowatts to microwatts range and can provide nominal power in standby or active modes to the medical implant circuitry while utilizing a portion of its generated power to trickle charge a secondary battery and/or a capacitor and/or another energy storage device. The secondary battery and/or capacitor and/or other energy storage device is capable of providing interim power that at times may be higher than the standalone betavoltaic power can supply (e.g. power bursts for radio telemetry, defibrillation etc.).

In yet another embodiment of this invention, a betavoltaic power source with a volumetric dimension of approximately 0.5 cubic centimeters or less supplies power in the nanowatts to microwatts level and can provide nominal current in standby or active modes to the medical implant circuitry while utilizing a portion of the current to trickle charge a secondary battery and/or a capacitor and/or another energy storage device with volumetric dimensions of approximately 0.5 cubic centimeters or less. The secondary battery and/or capacitor and/or other energy storage device is capable of providing interim power that may be higher than the standalone betavoltaic power supply (e.g. power bursts for radio telemetry, defibrillation etc.).

In one embodiment of this invention, either a Pm-147-based betavoltaic power source, or a tritium based betavoltaic power source, or another appropriate radioisotope power source with a volume that is less than approximately 0.5 cubic centimeters is constructed. The betavoltaic power source is in vivo, but is separate from or attached to the medical device/implant; and therefore must be bio-compatible. In this embodiment, a bio-inert package can be made from various materials such as ceramic, metals, alloys, polymers, combinations thereof, or other packaging materials known in the art. The betavoltaic power source may be sealed (hermetically or non-hermetically) within a cylindrical form factor (or another form factor appropriate for the intended application) that, in turn, allows currently available medical device delivery systems (e.g. catheters, stent delivery systems, syringe, etc.) to implant these devices in vivo. Similarly, the seal may be comprised of a bio-inert material known in the art. In some cases, the package may be sealed with a resistance welder, seam sealer, ultrasonic welder, laser-welder or another method known in the art.

In one example of this embodiment, a secondary battery and/or a capacitor and/or another energy storage device may be integrated into the betavoltaic package.

In another example of this embodiment a secondary battery and/or a capacitor and/or another energy storage device may be integrated into the medical implant/device.

In yet another example of this embodiment a secondary battery and/or a capacitor and/or another energy storage device may be separate from both the betavoltaic and the medical implant/device.

In another embodiment, the betavoltaic power source is without a package and is inserted directly into the medical implant/device package. The medical device package then serves as the package for the betavoltaic power source. The betavoltaic power source is approximately 0.5 cubic centimeters or less. The medical device's packaging provides shielding of the emissions from the betavoltaic, and protection for the betavoltaic source from its environment.

In a slightly different embodiment, the betavoltaic source is in a package inside of the medical device/implant. The betavoltaic package may or may not be bio-inert and may or may not be hermetically sealed. In one example of this embodiment, a secondary battery and/or a capacitor and/or another energy storage device may be integrated into the betavoltaic source package.

In another example of this embodiment a secondary battery and/or a capacitor and/or another energy storage device may be integrated into the medical implant/device.

In yet another example of this embodiment a secondary battery and/or a capacitor and/or another energy storage device may be separate from both the betavoltaic and the medical implant/device.

The Pm-147 isotope is made free of Pm-146 via current methods known in the art (e.g., see U.S. Pat. No. 7,435,399) allowing the use of modest radiation shielding requirements (e.g., the use of a biocompatible metals/materials that are deemed sufficient to provide such modest radiation shielding). This situation is in stark contrast to the original Betacel Pm-147 betavoltaic power supply for cardiac pacemakers, as described elsewhere herein, that requires considerable shielding due to the concomitant Pm-146 component.

In addition, the Pm-147 can be formed as a bidirectional radiation source using methods known in the art. The semiconductor collector (e.g., a p/n junction) may be constructed from a silicon-based material or from other semiconductor materials known in the art (such as GaAs, GaP, InAlP, InAlGaP, InGaP, GaN, SiC, etc).

In one example, the semiconductor collector comprises a type III-V material such as GaAs. GaAs has a relatively high diffusion length for its minority carriers but still requires the growth of multiple junctions to capture a majority of the electron-hole pairs (EHPs) generated via the beta particles impinging on the semiconductor collector.

FIG. 1 illustrates a triple-junction device (that is, three p/n regions 30, 32 and 34) where EHPs may be collected throughout the collector's volume. Each junction can be made between 15-20 microns thick or another appropriate dimension that optimizes the collection efficiency. It is estimated that Pm-147 beta particles can travel approximately 60 microns or more into a GaAs semiconductor. The junction thickness and the number of junctions can be optimized based on the use of different semiconductor collector materials and for different applications. The three vertical dashed lines in FIG. 1 each denote a boundary between a p region and an n region; the larger region in each of the three p/n regions 30, 32, and 34 can be either a p region or an n region (e.g. p regions 30A, 32A, and 34A, and n regions 30B, 32B, and 34B).

In another embodiment of a Pm-147 betavoltaic power source, two triple junction GaAs collectors (or constructed from other suitable materials) are constructed with a Pm-147 bidirectional source in the middle forming a unit. Both triple junctions are placed in intimate contact with Pm-147 source and are electrically connected in parallel. In one embodiment, a GaAs triple junction collector is constructed in a circular arrangement with a diameter of about 0.4 centimeters and a thickness of about 120 microns. Each p/n region interface forms a junction so three p/n interfaces form a triple junction, as depicted in FIG. 1. This technique is used in solar cells today in order to capture different wavelengths of light based on their penetration depth into solar cells.

Figure 2:
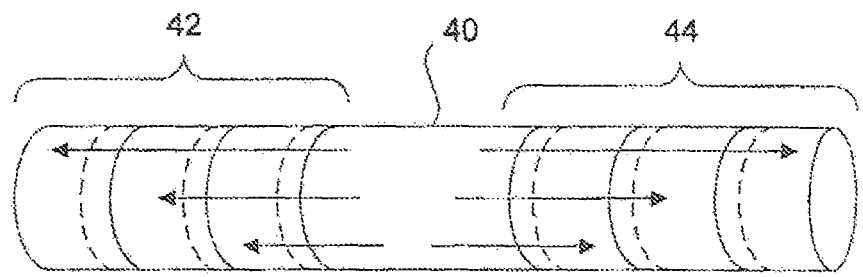
FIG. 2 illustrates a bi-directional betavoltaic cell.

FIG. 2 illustrates such a device with a source 40 between triple junctions 42 and 44. Each junction is approximately 15-20 microns thick and the Pm-147 bidirectional source is approximately 6 milligrams per square centimeter at 400 Curies per gram or 2.4 Curies per square centimeter. The combined bidirectional unit of FIG. 2 comprises 1.0 square centimeter and yields an open circuit voltage of 2.4 volts and a short circuit current of 14 microamps generating approximately 27 microwatts of power at beginning-of-life (BOL) with a fill-factor of approximately 80 percent. The half-life of Pm-147 is approximately 2.62 years and it should be noted that many medical devices have a useful lifetime of 3-5 years, thereby permitting use of a Pm-147 device.

Note that the thickness of the individual regions within each of the triple junctions 42 and 44 increases with increasing distance from the source 40 to account for the attenuation of the beta particle flux at increasing distances from the source. The arrowheads in FIG. 2 represent the beta particle flux. Generally, the thickness of the individual regions is selected so that about the same current is produced within each individual region. The individual regions (or cells since each region produces a current) within the triple junction 42 are in series and the individual regions within the triple junction 44 are in series. But the triple junction 42 may be connected in series or in parallel with the triple junction 44.

The FIG. 2 embodiment is shown in an elongated representation; in another embodiment, the source 40 and the junctions 42 and 44 are each shorter and thus the combination appears more disc-like than the tubular or cylindrical representation of FIG. 2.

The power density for this betavoltaic device 40 is approximately 5 milliwatts per cubic centimeter with an energy density of approximately 125 Watt-hours per cubic centimeter when integrated over two half-lives (5.24 years). To modulate the power outputs from the Pm-147 betavoltaic source, two bidirectional units may be placed in series to yield an open circuit voltage of 4.8 Volts with a short circuit current of 14 microamps at BOL.

The two bidirectional units may be connected to a secondary LiPON battery, a capacitor, or another energy storage device configuration to receive a trickle charge and subsequently discharge/provide higher power over a duty cycle or on-demand. By combining one or more LiPON batteries within a small cubic millimeter scale volume, the power emanating from the Pm-147 betavoltaic units can be varied freely from the nanoamp up to the maximum current output (e.g. Amp-seconds) as demanded by the platform. The approximate dimensions for this assembly, comprising two bidirectional Pm-147 sources, four betavoltaic collectors, and the LiPON batteries, is 0.05 cubic centimeter.

Rechargeable thin-film LiPON batteries may be purchased from Cymbet Corporation of Elk River, Minn. or Infinite Power Solutions from Littleton, Colo. LiPON batteries are robust over 10,000 charge/discharge cycles and have a low discharge rate of 3-6% even at human body temperatures. LiPON batteries can be discharged at rates of 10 C (i.e., discharged at ten times the battery's rated capacity) and in short bursts up to 40 C without deleterious effects upon its capacity or performance. For instance, in the case of a battery with 50 microamp-hour capacity it is possible to discharge at 1 C. This would be a 1 hour discharge at a rate of 50 microamps per hour, continuous. Or it can be discharged at 40 C for a short period, at a rate of 2 milliamps.

Cymbet Corporation's LiPON batteries can be fabricated with form factors well within cubic millimeter dimensions and with energy capacities of 1-50 microamp-hours. Infinite Power Solutions' batteries have capacities in the sub-milliamp-hour range, but they demonstrate a larger form-factor with linear dimensions measuring in the centimeter range and thicknesses of 180 microns. However, these batteries are sufficiently malleable to conform to cylindrical shapes. It should be noted that custom LiPON batteries with various dimensions and capacities can also be fabricated as desired.

In another embodiment, a tritium-based betavoltaic collector cell involving a III-V semiconductor, such as the structures described in the commonly-owned U.S. Pat. No. 8,487,507, entitled Tritium Direct Conversion Semiconductor Device and incorporated herein by reference in its entirety, is utilized.

In one embodiment, the dimensions are approximately 0.5 cm×0.5 cm or smaller per betavoltaic collector layer. Other embodiments may have larger dimensions. Additionally, the betavoltaic layers may be constructed with an approximate 0.5 cm diameter or smaller to optimally fit into cylindrical medical devices that can be implanted via a catheter-like delivery system. The thickness of the betavoltaic cell is approximately 10-25 microns or less with a tritium metal tritide layer (e.g. titanium, scandium, magnesium, lithium, palladium, etc.) having a thickness approximately ranging from less than 100 nanometers to greater than 1.0 micron, that is placed in contact with the active surface of the betavoltaic cell.

In other embodiments, betavoltaic cells within an approximate range of 25-180 microns thick may be used in medical implants by combining a high beta-flux magnesium alloy tritide, as described in the provisional patent application filed on Dec. 19, 2016, assigned application No. 62/435,907, and entitled Binary Intermetallic Hydrides as a Tritium Beta Emitting Source and/or using series and/or parallel stacking configurations as described in the provisional patent application filed on May 22, 2016, assigned application No. 62/339,943, and entitled Series and Parallel Connected Betavoltaic Cell Devices.

Other non-limiting examples of betavoltaic collector cells are described in commonly-owned U.S. Pat. No. 9,466,401, entitled Tritium Direct Conversion Semiconductor Device; the patent application filed on Feb. 17, 2015, assigned application Ser. No. 14/623,861, and entitled Tritium Direct Conversion Semiconductor Device For Use With Gallium Arsenide or Germanium Substrates; and any continuation application and continuation-in-part applications based on the patent references cited herein. Each of these patent references is incorporated herein in its entirety.

In certain ones of the various embodiments described herein directly and by reference, relatively thin III-V betavoltaic cells may utilize an epitaxial-lift-off process (an ELO process) or are constructed by etching away at least a portion of the substrate coupled with a back metallization to offer conduction and physical support of the cell.

Additionally, the thin III-V betavoltaic cells may use a metal tritide layer as back metallization via the deposition of candidate metal tritide forming metals or combination of metals as described elsewhere herein. These metals may be deposited through evaporation, sputtering or other methods known in the art. The metal tritide back metal offers support to the thin betavoltaic cell and an additional source of beta-flux through the back-side of the betavoltaic cell, thereby increasing electron-hole pair generation and the overall production of electrical power.

It should be noted that the metal tritide metal may, in some instances, present insulating properties due to the tritium in the metal matrix. In such cases, to ensure good current/voltage related properties, when convenient or advisable, a portion of the backside metal may be formed of a conductive non-hydride-forming metal to provide electrical conduction for the betavoltaic cell. In order to achieve reasonable power densities, the cells may be stacked in series and/or parallel configurations with or without the aid of flexible circuit cards or other interposing members between some of the layers to make parallel connections or even series connections. See for example certain embodiments contained within the provisional patent application filed on May 22, 2016, assigned application No. 62/339,943, and entitled Series and Parallel Connected Betavoltaic Cell Devices.

In certain embodiments and for certain applications the betavoltaic cell may have thicknesses ranging from approximately 25 microns to 625 microns. For thicker betavoltaic cells (e.g. 25 microns to 625 microns or greater), in one embodiment the inventors propose to use a surface enhancement technique to raise the power density/energy density. Although, surface enhancement techniques may also be utilized in thinner betavoltaic cells (e.g. 25 microns or thinner). See for example, the commonly-owned patent application filed on Jun. 24, 2014, assigned application Ser. No. 14/313,953, and entitled Tritium Direct Conversion Semiconductor Device Having Increased Active Areas.

Another approach that may be used thins the back surfaces of the betavoltaic semiconductor substrates by etching, polishing, grinding, and/or other lapidary techniques known in the art. Betavoltaic cells may also be thinned down to less than 200 microns thick.

In some embodiments III-V betavoltaic structures may be grown on silicon wafers that may be thinned by techniques known in the art. A silicon wafer can provide a more economically priced substrate for growth of III-V betavoltaic cell structures than the traditional, but typically more expensive substrates such as GaAs, Ge, GaP, etc.

The scandium, titanium, magnesium, palladium, lithium, alloyed combination or other suitable tritide forming layer(s) (including polymers) may be metallurgically/physically placed on top of the betavoltaic cell by directly depositing on top of the betavoltaic cell's active area through methods known in the art (e.g. evaporation, electro-deposition, sputtering, etc.). Alternatively, the metal tritide layer may be deposited on a separate thin substrate (i.e., approximately 25 microns or less to approximately 500 microns or greater) that is mechanically connected to the betavoltaic cell's active area via pressure, epoxy, or spot welding.

In one embodiment, the inventors prefer to have the tritide metal layer evaporated onto the cell's active area rather than using a separate substrate. This allows the formation of a single monolithic piece that includes both the metal tritide and the betavoltaic collector.

In another embodiment, a betavoltaic cell comprises two separate components (a betavoltaic collector and a tritium metal tritide layer/foil), but generally this embodiment occupies more volume and is lower in both power and energy density than other embodiments described herein.

The metal tritide is formed by exposure to tritium gas at pressures approximately ranging from less than 0.01 to greater than 20 Bar and temperatures ranging approximately room temperature to 600° C. for durations ranging minutes to days. It should be noted that metal tritides can also be formed at temperatures and pressures outside of the above-mentioned ranges and can also be formed through chemical and electrochemical reactions as is known in the art.

A cap layer of palladium ranging from approximately 1.0 nanometer to approximately 500.0 nanometers may be deposited over a scandium, titanium, magnesium, lithium, or another suitable metal, alloy or a combination of layers, to reduce the tritium loading temperature and stabilize the tritium within the metal matrix after the tritide has been formed. The palladium cap layer functions primarily as a catalyst and serves to provide an expedited rate of reaction for inducing the process of tritiation; palladium has an additional benefit for the tritiation process in that it can facilitate tritium loading of a metal tritide at significantly lower temperatures and pressures compared to processing efforts conducted in the absence of palladium.

This subsequent increase in the kinetics of the tritiation process induced by the palladium cap layer does not alter the functionality of the betavoltaic cell, and it is usually deposited directly upon un-passivated surfaces (i.e., surfaces containing no oxide barriers to tritiation) of metal/alloy hydride storage layers (e.g. scandium, titanium, magnesium, lithium, or another suitable metal, alloy, or combination of layers. The palladium layer is typically laid down in a vacuum/inert gas atmosphere process, in order to eliminate oxygen contamination and is deposited via any of the metal deposition techniques described elsewhere herein.

It should also be noted that the metal tritide layer may also be formed via an in-situ evaporation of the metal in the presence of gaseous tritium.

The average current produced in a type III-V semiconductor in the presence of the metal tritide is approximately 1.0 to 6.0 nanoamps per square millimeter or 100-600 nanoamps per square centimeter. These values may be increased or reduced depending on the embodiment, including at least any of the several embodiments described herein. The open circuit voltage for a type III-V structure ranges between 0.4 Volts to 1.2 volts, but again may be higher or lower in some configurations and embodiments.

Betavoltaic cell layers may be stacked vertically and configured in series or parallel using current-channeling interposers (e.g., flexible circuit cards or yttria-stabilized zirconia dielectric materials) between betavoltaic cells or groups of cells, through the application of novel etching and metallization techniques (as described in the commonly-owned patent application filed on May 22, 2016, assigned application No. 62/339,943, and entitled Series and Parallel Connected Betavoltaic Cell Devices) or using other techniques known in the art. It should be noted that various stacking configurations (serial, parallel, or combinations thereof) produce different voltage and current outputs from the betavoltaic composite device.

In one example, a tritium betavoltaic device is comprised of a plurality of cells, each cell 10 microns thick. Each cell comprises at least one p/n junction with a tritium source, and each cell(s) is connected to the proximate cell(s) with through-vias for electrical connections. Each betavoltaic cell consists of a type III-V semiconductor material, as described in particular in the commonly-owned U.S. Pat. No. 8,487,507 as referred to elsewhere herein and as described in the other commonly-owned patent references cited herein) and a tritium metal tritide deposited on its surface producing a short-circuit current of about 300 nanoamps per square centimeter at BOL (beginning of life) and a voltage of 0.9 volts per cell layer with a fill-factor of approximately 80%. As is known to those skilled in the art, the fill factor is a figure of merit for use with semiconductors. The fill factor is a ratio of performance of a cell compared to that of an idealized cell. Then the power of a cell is equal to the short circuit current times the open circuit voltage times the fill factor. A cell with a fill factor of 80% produces 80% of the "maximum theoretical power."

A betavoltaic device can be made with a variety of form factors ranging from cubic millimeter volumes or greater and varying geometries (e.g., cylindrical). In one embodiment, the power density is approximately 216 microwatts per cubic centimeter at BOL and 15 Watt-hours per cubic centimeter when integrated over one tritium half-life (12.3 years).

The application sets forth example dimensions for a betavoltaic source and its constituent elements. However, variations from the recited dimensions provide useful sources with desirable operating properties. For example, a 150-micron thick cell may still be useful in certain applications. See, for example, a commonly-owned patent application filed on Jun. 24, 2014, assigned application Ser. No. 14/313,953, and entitled Tritium Direct Conversion Semiconductor Device Having Increased Active Areas describes enhanced surface area cells. In this case, the cell may be 150 microns thick but it may have an effective area of ten times that amount due to valleys/trenches formed to create enhanced surfaces.

In another embodiment, a thick betavoltaic cell (e.g., 50 microns, 80 microns, 150 microns, 200 microns, etc.) may be useful in a configuration where a high-end metal tritide alloy such as a Mg alloy (see the commonly-owned patent application filed on Dec. 19, 2016, assigned application No. 62/435,907 and entitled Binary Intermetallic Hydrides as a Tritium Beta Emitting Source, in combination with the thick betavoltaic cell produces current in the ranges of greater than 200 nanoamps/cm^2.

Additionally, if a higher bandgap III-V betavoltaic cell (e.g. InAlP) is utilized, an open circuit voltage of approximately 1.2 volts or greater may be achieved. These elements, when combined together, can produce a moderate power density betavoltaic with applications for medical implants especially where stacking configurations and series/parallel connections, as referred to herein, are utilized.

Similar to the Pm-147 betavoltaic embodiment, a 1-50 microamp-hour LiPON secondary thin-film battery may be connected to the composite tritium betavoltaic device to vary freely from nanoamp to milliamp ranges. Furthermore, other secondary battery, capacitor, and/or energy systems may be utilized in lieu of the LiPON battery.

A hybrid betavoltaic comprised of tritium betavoltaic layers that trickle charge a LiPON battery, a capacitor, and/or another energy storage system can be used to power leadless pacemakers requiring average continuous power draw of approximately 5-30 microwatts for over 12 years within a volume of approximately 0.1 cubic centimeters. This represents a factor-of-ten reduction in volume, being approximately one tenth the size of the smallest leadless pacemaker batteries currently in existence today, without sacrificing energy density, capacity, or power output performance.

The application sets forth example dimensions for various betavoltaic sources and their constituent elements. However, variations from the recited dimensions may provide useful sources with desirable operating properties. For example, a hybrid betavoltaic power source with 0.5 cubic centimeters or greater volume may be desired in certain applications. For instance, a small betavoltaic source with secondary energy systems that may be larger than 0.5 cubic centimeters are useful in certain applications.

In another example, this composite tritium betavoltaic's form factor may be constructed with dimensions of 1.5 mm×2.0 mm×0.15 mm producing 0.1 microwatts of power at BOL and can easily trickle-charge a 1.0 microamp-hour LiPON battery measuring 1.5 mm×1.3 mm×0.15 mm. This small form factor hybrid tritium betavoltaic can supply power for an ultra-low-power microcontroller with a pressure sensor such as the implantable cubic millimeter ocular-implant wireless pressure sensor for glaucoma patients described above.

The hybrid tritium betavoltaic cell may be physically bonded to the cubic millimeter wireless pressure sensor comprising a microcontroller, memory, analog-digital converter, pressure sensor, and wireless transceiver to achieve a cubic millimeter scale device structure.

Figure 3:
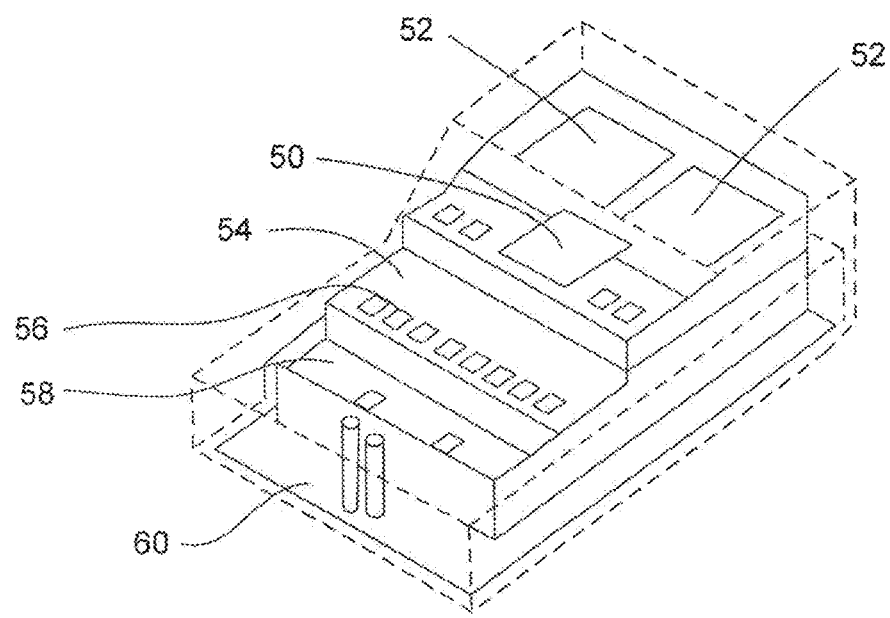
FIG. 3 illustrates use of a betavoltaic battery in an implantable device.

FIG. 3 illustrates such a device comprising a hybrid tritium betavoltaic 50, a wireless transceiver 52 for sending and receiving signals from an external device, an A/D and/or D/A converter 54, a processor and memory elements 56, a chargeable power source 58, and a MEMS pressure sensor 60. In one embodiment, the structure of FIG. 3 is about 0.5 mm×2 mm×1.5 mm.

The hybrid tritium betavoltaic source supplies power and energy capacity for operating in any area of the body for over a decade without the need for light collected via a solar cell.

As a note, the invention is not limited to the cubic millimeter volume set forth in FIG. 3 and can be made using other ultra-low power cubic millimeter devices known in the art.

Applications for the present invention are also not limited to pressure and temperature sensing but can make use of other ultra-low power sensing devices. In addition, it can be used for therapeutic purposes such as dispensing medication from an on-chip dispenser that can be implanted in a strategic dosing location.

It should be noted that cubic millimeter scale ultra-low power devices can vary in power consumption depending on configuration, duty cycle and sensor capabilities. However, the hybrid tritium-based betavoltaic can meet varying current and voltage requirements via stacking and electrical connection configurations. Similar betavoltaics with higher power in the range of microamps may be made with other radioisotopes such as Pm-147.

The hybrid tritium betavoltaic coupled to the pressure sensor of FIG. 3 can also be used in non-medical, external environments such as in mesh sensor networks (e.g. dust networks where dust-sized sensors communicate with each other).

A betavoltaic cell of the present invention can also be used in conjunction with radioactive implantable seeds that irradiate tumors. Such a system can provide daily monitoring of a tumor and can provide information of the tumor's size change via changes in pressure. This approach can also be used with chemotherapy in-lieu of the radioactive seed. This type of wireless sensor can also be used in stents to measure pressure/strain changes that would actively monitor scar-tissue growth.

In another embodiment, the semiconductor collector's surface may be enhanced to increase the surface area of the collector. An increase in surface area provides an increase in power production ranging from approximately 2 to 100 times the power produced from a planar surface betavoltaic semiconductor collector. Semiconductor collector surface structures with increased surface area and power production are described in the commonly-owned patent application filed on Jun. 24, 2014, assigned application Ser. No. 14/313,953, and entitled Tritium Direct Conversion Semiconductor Device Having Increased Active Areas.

In all embodiments, the specified radioisotope may be exchanged for other beta-emitting radioisotopes known in the art. In addition, other radioisotopes or combinations of radioisotopes and/or substrates whose end-product is an electron or beta particle that impinges on the semiconductor may be utilized.

The radioisotope may be selected to optimize power vs. longevity and/or cost or availability. For example, Phosphorus-33 is a short-lived beta-emitting radioisotope with a half-life of 25.3 days and has an energy spectrum that approximates that of Promethium-147. The advantage over Promethium-147 is that it is readily available and less expensive and may be appropriate for certain short-lived applications (e.g. short-lived medical implant sensors).

The increased surface area of the semiconductor collector may be used with or without the thin semiconductor epi-layers described in this patent application and in the commonly-owned patent application filed on Dec. 14, 2009, assigned application Ser. No. 12/637,735 and entitled Tritium Direct Conversion Semiconductor Device having Increased Active Area. Increased surface area semiconductor collectors can increase the energy density of betavoltaics by up to 100 times or greater over planar semiconductor surfaces. Additionally, the enhanced surface area reduces the overall cost of betavoltaic devices by reducing the semiconductor area necessary to power devices.

According to the certain embodiments of the present invention, it comprises one or more beta sources coupled to betavoltaic collectors. The arrangement can be as simple as a two-dimensional beta source and betavoltaic collector connected to a secondary battery, capacitor, and/or another secondary energy storage unit.

In another configuration, the beta sources/collectors can be configured in series or parallel to trickle charge the secondary cell or battery while the secondary cell or battery may be utilized for power bursts or high power usage periods. The betavoltaic cell or battery can also utilize a portion of its power to supply electrical systems without the aid of the secondary energy storage unit.

Figure 4:
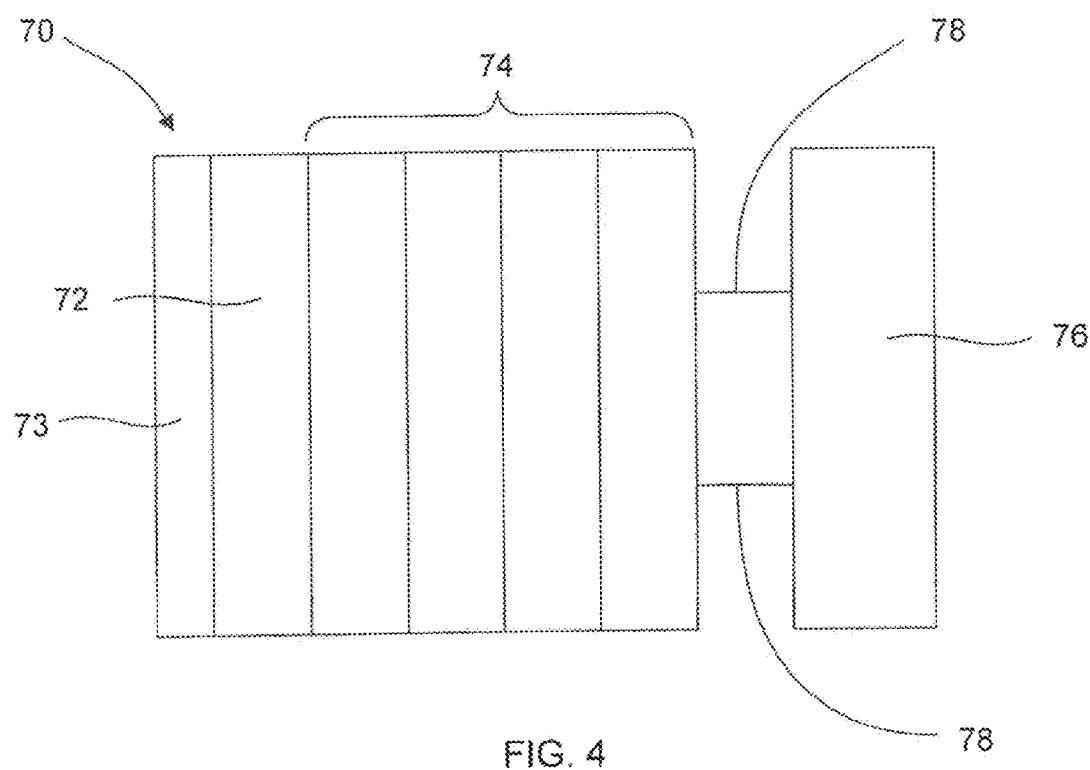
FIG. 4 illustrates a betavoltaic battery of the present invention.

FIG. 4 illustrates a betavoltaic battery 70 comprising a source of beta particles 72, regions 74 for collecting the beta particles, and secondary power source 76 charged by the electron-hole pairs generated within the region 74. In the illustrated embodiment, the secondary power source is connected to the regions 74 via conductors 78. In another embodiment (not illustrated) the secondary power source 76 is bonded to or in intimate contact with the regions 74 in lieu of utilizing the conductors 78.

Note that palladium can also form a metal tritide. However, it does not have as high a tritium content as, for example, a titanium tritide, scandium tritide, magnesium tritide, lithium tritide etc. However, a palladium cap layer prevents oxidation of the titanium, scandium, magnesium, lithium metal or other tritide metal/alloy layer(s) candidates below it, since these metals will readily oxidize when exposed to air and form an oxide barrier to tritium. It also dissociates the T2 (tritium two) molecule to elemental T allowing it to diffuse and bond to the metal hydride below it (e.g. titanium, magnesium, lithium, scandium etc.). The palladium also helps retain the tritium in the metal hydride below because it prevents oxygen from attacking the metal and releasing tritium species (e.g. tritium oxides, tritium metal oxides) into the surrounding environment. This makes the palladium layer useful when handling the tritium sources post-tritiation. It is helpful in the manufacturing process because of reduced tritium contamination.

FIG. 5 illustrates an embodiment of a betavoltaic battery 90 for implanting in a medical device. As shown in the cut-away view of FIG. 6, the battery 90 comprises current-generating cells 96, each further comprising a beta source 97 and at least one p/n junction 98.

FIG. 6 further illustrates the stacking arrangement of the cells 96 within a package 100. A conductor 102 connects a cell to a lid 100A of the package 100. A connection from a lowest cell to a base 100B of the package 100 is not visible. A dielectric disc 103 separates the lid 100A from the base 100B.

FIG. 7 illustrates a beta source 97 and a p/n region or n/p region 98, both components of the cells 96.

Returning to FIG. 5, the betavoltaic battery 90 charges a secondary power source 110 by supplying current through conductors 112.

In another embodiment not illustrated, the conductor 102 (insulated) is not connected to the package but instead exits the package for connection to the secondary power source.

As known by those skilled in the art, the secondary power source 110 is illustrated in a simplistic form as additional components may be required to manage operation of the secondary power source and supply power to a load, such as an implantable medical device.

In another embodiment two conductors may exit the lid of the betavoltaic power source with a conductive material comprising the package. The two conductors are isolated from each other with a dielectric material.

Other configurations for use with multiple beta sources are illustrated in the provisional patent application filed on May 22, 2016, assigned application No. 62/339,943, and entitled Series and Parallel Connected Betavoltaic Cell Devices, which is herein incorporated by reference.

While certain embodiments of the present invention have been shown and described herein, such embodiments are provided by way of example only. Numerous variations, changes and substitutions will occur to those of skilled in the art without departing from the invention herein. Accordingly, it is intended that the invention be limited only by the spirit and scope of the appended claims.

What is claimed is:

1. A betavoltaic power source comprising:
   a source of beta particles;
   a first doped region for collecting the beta particles and for generating electron hole pairs responsive thereto, the first doped region comprising a p region and disposed proximate the source of beta particles;
   a second doped region for collecting the beta particles and for generating electron hole pairs responsive thereto, the second doped region comprising an n region and disposed proximate the first doped region;
   a secondary power source charged by current developed by the electron hole pairs; and
   wherein the betavoltaic power source has a volumetric dimension of 0.5 cubic centimeters or less.

2. The betavoltaic power source of claim 1, wherein the power source comprises a secondary battery, a capacitor, or an energy storage device.

3. The betavoltaic power source of claim 1, wherein the source of beta particles comprises tritium (H-3), promethium-147 (Pm-147), or nickel-63 (Ni-63).

4. The betavoltaic power source of claim 1, wherein the source for emitting beta particles comprises a tritium metal tritide material.

5. The betavoltaic power source of claim 4, wherein the tritium metal tritide material comprises one or more of scandium, titanium, magnesium, palladium, and lithium.

6. The betavoltaic power source of claim 5, further comprising a palladium material layer disposed on a surface of the tritium metal tritide material.

7. A bio-inert package enclosing the betavoltaic power source of claim 1.

8. An implantable medical device comprising the betavoltaic power source of claim 1.

9. A pressure sensor bonded to the betavoltaic power source of claim 1 and receiving operating current from the secondary power source.

10. The betavoltaic power source of claim 1, wherein a material of the first and second doped regions comprises a type III-V material.

11. The betavoltaic power source of claim 1, wherein a material of the first and second doped regions comprises a GaAs material.

12. A device comprising:
    a source of beta particles;
    a plurality of regions for collecting the beta particles and for generating electron hole pairs responsive thereto;
    a power source charged by a current developed by the electron hole pairs;
    a wireless transmitter for sending signals to an external receiver, the wireless transmitter powered by the power source;
    a sensor for sensing a condition in an environment surrounding the device;
    the signals representative of the condition as measured by the sensor; and
    wherein the condition comprises at least one of pressure and the sensor comprises a MEMS pressure sensor, and temperature and the sensor comprise a temperature sensor, and strain and the sensor comprises a strain sensor.

13. The device of claim 12, wherein the power source comprises a secondary battery, a capacitor, or an energy storage device.

14. The device of claim 12, wherein the power source comprises a LiPON battery.

15. A betavoltaic power source comprising
    first and second spaced-apart beta particle sources; and
    first and second collecting regions for collecting the beta particles from the respective first and second spaced-apart beta particle sources and for generating electron hole pairs responsive thereto, the collecting regions disposed between the first and second spaced-apart beta particle sources.

16. The betavoltaic power source of claim 15 further comprising a secondary power source charged by the current developed by the electron hole pairs.

* * * * *